United States Patent [19]

Schneider

[11] Patent Number: 5,098,381
[45] Date of Patent: Mar. 24, 1992

[54] CATHETER FOR RECANALIZING CONSTRICTED VESSELS

[75] Inventor: Ernst Schneider, Zurich, Switzerland

[73] Assignee: Schneider Europe, Zurich, Switzerland

[21] Appl. No.: 732,953

[22] Filed: Jul. 19, 1991

Related U.S. Application Data

[63] Continuation of Ser. No. 617,436, Nov. 19, 1990, abandoned, which is a continuation of Ser. No. 339,556, Apr. 17, 1989, abandoned.

[30] Foreign Application Priority Data

Apr. 20, 1988 [CH] Switzerland .................. 1460/88

[51] Int. Cl.$^5$ ................. A61M 29/00; A61M 25/00
[52] U.S. Cl. .............................. 604/96; 606/194
[58] Field of Search ............ 604/96, 97, 98, 99, 604/100, 101, 102, 103, 104; 606/191, 194; 128/207.15

[56] References Cited

U.S. PATENT DOCUMENTS

| | | | |
|---|---|---|---|
| 1,738,152 | 12/1929 | Porter | 604/104 |
| 1,852,351 | 4/1932 | Lewis | 604/96 |
| 2,470,665 | 5/1949 | Stiehl | 604/96 |
| 3,173,418 | 3/1965 | Baran | 604/101 |
| 4,417,576 | 11/1983 | Baran | 604/101 |
| 4,423,725 | 1/1984 | Baran et al. | 604/101 |
| 4,437,856 | 3/1984 | Valli | 604/96 |
| 4,824,436 | 4/1989 | Wolinsky | 604/53 |
| 4,994,033 | 2/1991 | Shockey et al. | 604/101 |

FOREIGN PATENT DOCUMENTS 8912478 12/1989 PCT Int'l Appl. ........... 604/104

Primary Examiner—John D. Yasko
Assistant Examiner—William W. Lewis
Attorney, Agent, or Firm—Peter C. Richardson; Lawrence C. Akers; Thomas C. Naber

[57] ABSTRACT

A catheter for treating an obstructed blood vessel comprises an elongated tubular body having an internal lumen, a proximal portion and a distal portion, and includes an inflatable dilatation element on the distal portion thereof. The dilatation element is in communication with the lumen and is adapted to be inflatable and deflatable by the application of a suitable therapeutic tissue dissolving fluid pressurized within the lumen. The dilatation element includes a wall having microporus openings adapted to be permeable by the fluid applied to inflate the dilatation element. The fluid, which is pumped into the interior space of the dilatation element, under sufficient pressure, presses through the microporus wall directly on and into the adjacnet tissue. The fluid tends to dissolve the tissue, thereby treatment time is considerably shortened and the long-term success of the treatment is improved, since the impairing tissue is not only dislodged but also dissolved from the vessel.

8 Claims, 1 Drawing Sheet

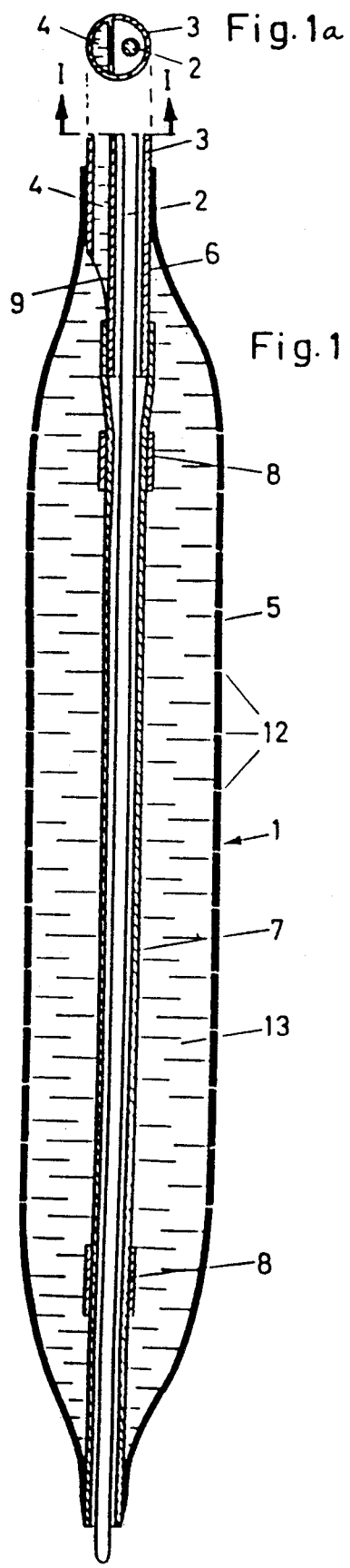
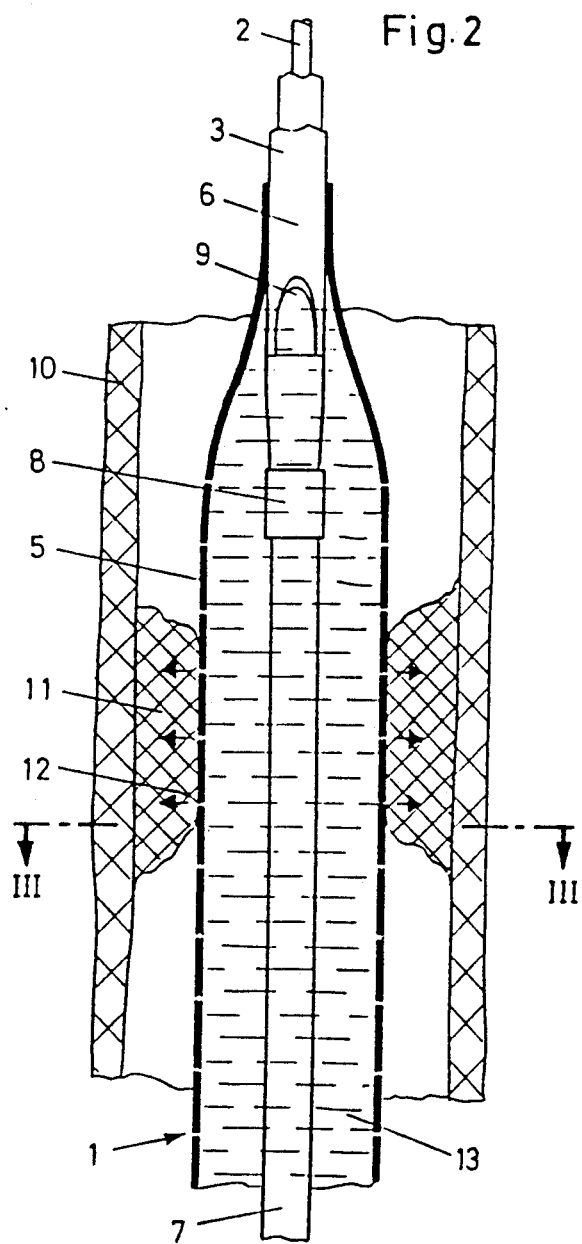
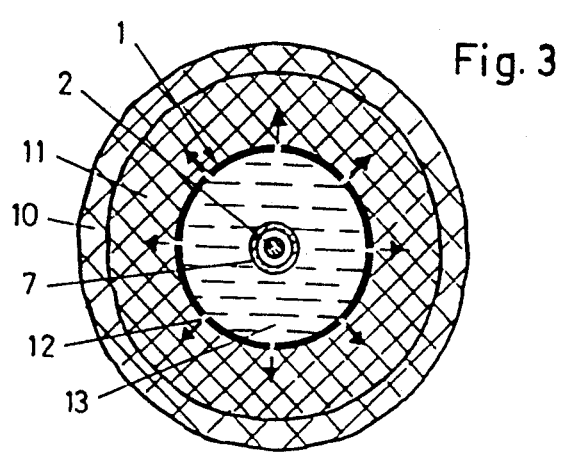

CATHETER FOR RECANALIZING CONSTRICTED VESSELS

This is a continuation of application Ser. No. 617,436, filed on Nov. 19, 1990, which is a continuation of application Ser. No. 339,556, filed on Apr. 17, 1989 both now abandoned.

BACKGROUND OF THE INVENTION

The invention relates to a dilatation catheter for treating a constricted blood vessel. Dilatation catheters have been employed for some time in the treatment of vascular obstructions generally known as angioplasty. Such catheters have an elongated tubular body with a balloon at the distal end that is inflatable and deflatable under fluid pressure. A guide wire is typically first inserted within the vessel to the location of the constriction. The catheter is then inserted (with the balloon deflated) over the guide wire with the balloon positioned at the location of the constriction. By way of an externally accessible internal lumen leading through the support tube, the balloon is filled with fluid, so that it expands causing the occluding tissue to be pressed outwardly into the vessel wall.

A disadvantage of the angioplasty procedure is that the treatment of severe constrictions takes a comparatively long time and can require periodic interruption in order to avoid distal ischemia. It has also been found that the treatment is sometimes unsuccessful because the occluding tissue is not removed but merely pressed to the wall of the vessel and restenosis can eventually occur. The success of such a treatment can be improved if a substance that will dissolve the impairing tissue, as for example a plasminogen activator, is introduced into the vessel to be treated.

SUMMARY OF THE INVENTION

It is an object of the present invention to provide a dilatation catheter in which vascular constrictions can be treated with a suitable therapeutic (tissue dissolving) fluid resulting in greater long-term success.

This object is achieved by the present invention in which a catheter for treating an occluded blood vessel comprises an elongated tubular body having an internal lumen, a proximal portion and a distal portion, and includes an inflatable dilatation element on the distal portion thereof. The dilatation element is in communication with the lumen and is adapted to be inflatable and deflatable by the application of a suitable tissue dissolving fluid pressurized within the lumen. The dilatation element includes a wall having microporus openings adapted to be permeable by the fluid applied to inflate the dilatation element. The fluid, which is pumped into the interior space of the dilatation element, under sufficient pressure, presses through the microporus wall directly on and into the adjacent tissue. The fluid tends to dissolve the tissue, thereby treatment time is considerably shortened and the long-term success of the treatment is improved, since the impairing tissue is not only dislodged but also dissolved from the vessel. The fluid has a rapid and focused effect because it is brought directly to the action site and thereby requires only a minimal quantity of the therapeutic fluid.

BRIEF DESCRIPTION OF THE DRAWINGS

The invention will be better understood from the following detailed description taken in conjunction with the drawing.

FIG. 1 shows a longitudinal section of the catheter of the present invention in the distended state;

FIG. 1a is a sectional view taken along the line I—I of FIG. 1;

FIG. 2 shows a longitudinal section of a blood vessel having the catheter of FIG. 1 inserted therein; and FIG. 3 is a sectional view taken along the line III—III of FIG. 2.

DETAILED DESCRIPTION OF THE INVENTION

Referring to the figures, the catheter of the present invention is illustrated, by an example, in which an elongated tubular body 3 has a dilatation balloon 1 attached to the distal end thereof. The interior of the dilatation balloon is in communication with an internal lumen 4 through an opening 9 of a connecting piece 6. The lumen 4 is accessible at the proximal portion of the body to inflate and deflate the balloon with a suitable fluid respectively by a typical suction and pressure pump (not shown).

The dilatation balloon 1 is deflated into a compressed or folded state for the purpose of introduction into a blood vessel. For such introduction of the dilatation balloon 1, a stenosed section of vessel (see FIG. 3) is first probed utilizing a well-known technique by a guide wire 2 and the catheter and the dilatation balloon 1 is then inserted onto the guide wire 2 and extended to the section of vessel to be dilated. Radiopaque marking elements 8 are mounted on a tubing piece 7 and are clearly visible on x-ray to facilitate the proper location of the balloon.

When the dilatation balloon 1 is in the desired location of the vessel, it is filled with a suitable therapeutic fluid 13 under controlled pressure by means of a pressure pump, until it assumes the cylindrical shape. The dilatation balloon 1 is designed so that after reaching a determined shape, it will not assume a larger diameter even when considerably greater pressure is exerted. This prevents the vessel from being inadvertently excessively distended and damaged.

The dilatation balloon 1 is formed for example, of polyvinyl chloride and has, a cylindrical wall 5 provided with microporus openings 12. The openings 12 are preferably arranged evenly in the radial and longitudinal surface so that in the dilated state, the fluid 13 presses uniformly radially outwardly through the wall 5. The openings 12 have a comparatively small diameter, for example 0.05 mm, so that the wall 5 is microporus yet permeable to the fluid 13.

In FIGS. 2 and 3, the obstructions is schematically illustrated as a tissue 11 forming a stenosis in vessel 10. In the dilated state, the outer surface of the wall 5 lies adjacent to the tissue 11 and the fluid 13 is forced into the tissue 11 through the openings 12. The fluid 13 is thus delivered directly to the tissue 11.

The openings 12 are uniformly distributed on the wall 5 at approximately the same intervals, in order to ensure a suitably uniform and distributed delivery of the fluid 13 to the tissue 11.

The fluid 13 contains a suitable therapeutic agent and contrast medium. In the case of treatment of a occlusion the therapeutic agent is specifically a drug which dissolves the tissue 11. Such drugs are known for example as lytic agents such as plasminogen activator; although substances other than lytic agents can also be effective. During treatment the vasoconstrictive tissue 11 is pressed onto the vascular wall 10 and simultaneously a specified amount of the therapeutic fluid is introduced under pressure directly into the tissue 11. The constricting tissue 11 can thus be eliminated in a fast and gentle manner.

I claim:

1. A catheter for treating an obstructed blood vessel, said catheter comprising an elongated tubular body having a proximal tubular body portion, a distal tubular body portion, and a common internal lumen extending through both of said body portions, the internal lumen, and a single inflatable dilatation element whereby said dilatation element is in communication with said internal lumen and inflatable and deflatable by the application of a pressurized fluid within said lumen, and wherein said dilatation element has a single wall having microporous openings there through to the exterior of the catheter which are permeable to the fluid applied to inflate said dilatation element.

2. A catheter according to claim 1, wherein said dilatation element comprises a tubular balloon having a substantially cylindrical wall when inflated.

3. A catheter according to claim 2 which said microporus openings are arranged radially.

4. A catheter according to claim 2 wherein said microporus openings are distributed substantially uniformly along the cylindrical wall.

5. A catheter according to claim 2 wherein said microporus openings are approximately 0.05 mm in diameter.

6. A catheter according to claim 5 wherein said dilatation element is formed of polyvinyl chloride.

7. A catheter according to claim 2 wherein said elongated tubular body further includes a second lumen adapted to receive a guide wire.

8. A method of treating a obstructed blood vessel utilizing a catheter as defined in claim 1, comprising the following steps:

locating the dilatation element of the catheter at a desired location adjacent the constrictive tissue in the blood vessel;

pressurizing the dilatation element with a suitable therapeutic fluid whereby the dilatation element expands compressing the constrictive tissue and the therapeutic fluid permeates through the microporus openings and into the constrictive tissue to facilitate dissolving the tissue.

* * * * *